US00PP10695P

United States Patent [19]

Nicholson

[11] Patent Number: Plant 10,695

[45] Date of Patent: Nov. 17, 1998

[54] *GERANIUM PRATENSE* PLANT NAMED 'SUMMER SKIES'

[75] Inventor: Kevin Nicholson, Wisbech, England

[73] Assignee: Blooms of Bressingham Ltd., Norfolk, England

[21] Appl. No.: 799,002

[22] Filed: Feb. 7, 1997

[51] Int. Cl.[6] ..... A01H 5/00

[52] U.S. Cl. ..... Plt./87.12

[58] Field of Search ..... Plt./87.12

*Primary Examiner*—Elizabeth C. Kemmerer

*Attorney, Agent, or Firm*—Foley & Lardner

[57] ABSTRACT

A new and distinct cultivar of *Geranium pratense* plant named 'Summer Skies', characterized by its double violet blue blossoms that have a hint of white, flowering which continues from mid-June to early August, compact bushy clumps, dull green foliage, and its use in borders or containers.

1 Drawing Sheet

The present invention relates to a new and distinct cultivar of hardy perennial herbaceous plant of the genus Geranium, a member of the Geraniaceae family, and the species *G. pratense,* and referred to by the cultivar name 'Summer Skies'.

This new cultivar of Geranium is a seedling from a cross between *Geranium pratense* 'Stratum', the male or pollen parent, and the Geranium cultivar 'Spinners,' the female or seed parent. The cross was made as part of a breeding program carried out by the inventor Kevin Nicholson in Wisbech, Cambridgeshire, England. The new cultivar was selected by the inventor in 1996 from the progeny of the cross by virtue of its vigorous leafy growth and fully double flowers.

The first act of asexual reproduction of 'Summer Skies' was accomplished after selection when vegetative cuttings were taken from the new cultivar by the inventor in a controlled environment at Wisbech, Cambridgeshire, England. Examination of plants grown from these cuttings has demonstrated that the combination of characteristics as herein disclosed for 'Summer Skies' are firmly fixed and are retained through successive generations of asexual reproduction.

The new cultivar 'Summer Skies' has achieved the objective of the breeding program of providing a flowering perennial with quality flowers and foliage. The prolific double flowers make an excellent display of pale violet blue with a hint of white flowers from mid-June to early August. The new cultivar produces compact bushy clumps which flower for many weeks, starting in mid-June and continuing to early August. The finely cut, divided and somewhat dull green leaves make a pleasing backdrop to the double violet blue flowers. The plant thrives best in full sun and well drained soil. It does not succeed well in dry shade.

The flowers are of a classic Meadow Cranesbill flower shape and resemble those of Geranium *pratense* 'Striatum' in color only. 'Summer Skies' also bears a resemblance to *Geranium pratense* 'Plenum Caeruleum' and *Geranium pratense* 'Plenum Violaceum' in habit and in flower shape. However, the combined characteristics of 'Summer Skies' result in a unique new cultivar.

In the accompanying color photographic drawing, the photo is a close up view Showing the characteristics of 'Summer Skies' in detail.

DETAILED PLANT DESCRIPTION

The following is a detailed description of 'Summer Skies', with color determinations and comparisons being based on The Royal Horticultural Society (R.H.S.) Colour Chart.

Classification:

*Orgin.*—Seedling selection from progeny of cross between *Geranium pratense* 'Striatum' and Geranium 'Spinners'.

Plant:

*Habit.*—Compact bushy clumps.

*Size.*—Mature plants are 60cm in height with a spread of 60cm.

*Root System.*—Fibrous.

*Plant vigor.*—A perennial that shows vigorous and healthy growth throughout Great Britain.

*Blooming habit.*—Borne on flower stems that arise from the base of the plant. Flowers are double.

*Blooming period.*—From mid-June continuing into early August.

*Hardiness.*—Winter hardy throughout the British Isles. the plant has not been fully tested for maximum summer tolerance above 32° C. (90° F.).

Foliage:

*Arrangement.*—Petiole arising from base of plant.

*Type.*—Deeply cut, compound leaves.

*Length.*—25 cm.

*Width.*—25 cm.

*Petiole length.*—20 cm.

*Margins.*—Parted.

*Apex.*—Acute.

*Base.*—Sagittate.

*Color.*—Mature leaves, upper surface 137A, under surface 137B.

Flowers:

*Petals.*—20–30 in number, of varying size. Petals are slightly veined.

*Flower shape.*—Saucer shaped.

*Flower size.*—30 mm diameter.

*Carpels.*—5 celled.

*Stamens.*—Small.

*Color.*—Mature petals, 84C to 73D, with a hint or slight infusion of greenish white 157D.

I claim:

1. A new and distinct cultivar of *Geranium pratense* plant named 'Summer Skies' as illustrated and described.

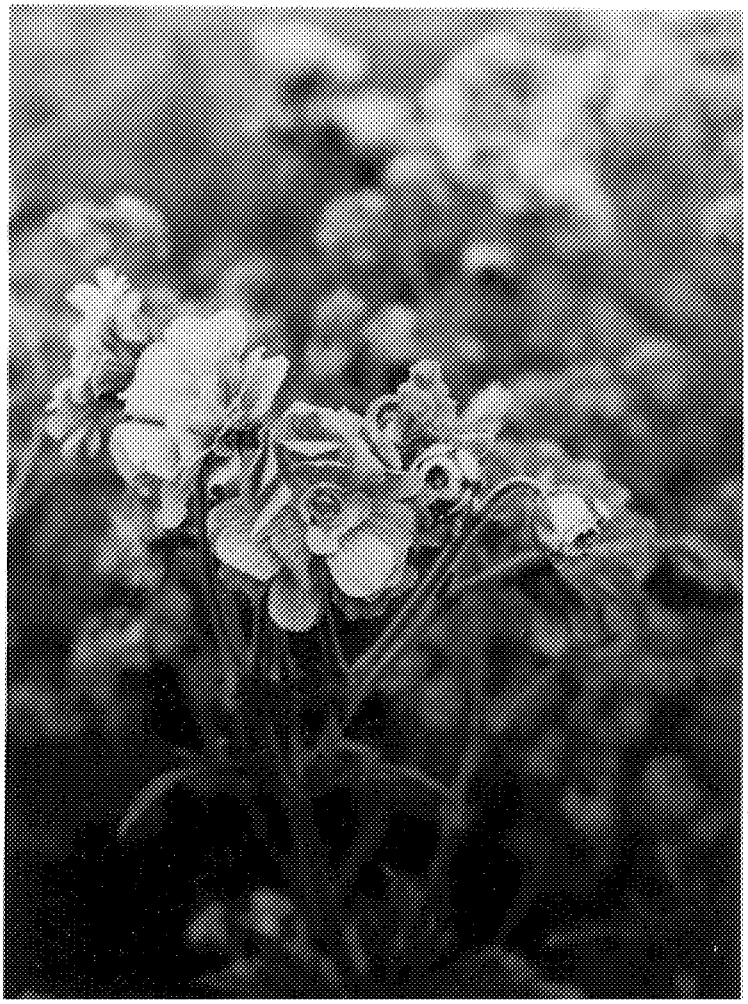

* * * * *